United States Patent [19]

Rogozinski

[11] Patent Number: 5,607,425
[45] Date of Patent: Mar. 4, 1997

[54] APPARATUS, METHOD AND SYSTEM FOR THE TREATMENT OF SPINAL CONDITIONS

[76] Inventor: Chaim Rogozinski, 3223 Front Rd., Jacksonville, Fla. 32256

[21] Appl. No.: 479,834

[22] Filed: Jun. 7, 1995

Related U.S. Application Data

[63] Continuation of Ser. No. 131,947, Oct. 8, 1993, abandoned.

[51] Int. Cl.$^6$ .............................. A61B 17/56; A61B 17/58
[52] U.S. Cl. ................................................. 606/61; 606/60
[58] Field of Search ................................. 606/60, 61, 69, 606/71, 72, 73

[56] References Cited

U.S. PATENT DOCUMENTS

| | | |
|---|---|---|
| 4,041,939 | 8/1977 | Hall . |
| 4,085,744 | 4/1978 | Lewis et al. . |
| 4,361,141 | 11/1982 | Tanner ..................................... 606/61 |
| 4,743,260 | 5/1988 | Burton ..................................... 606/61 |
| 4,771,767 | 9/1988 | Steffee . |
| 4,865,604 | 9/1989 | Rogozinski . |
| 5,000,166 | 3/1991 | Karpf . |
| 5,030,220 | 7/1991 | Howland . |
| 5,092,893 | 3/1992 | Smith ..................................... 606/60 |
| 5,102,412 | 4/1992 | Rogozinski ................................. 606/61 |
| 5,129,899 | 7/1992 | Small et al. . |
| 5,129,900 | 7/1992 | Asher et al. . |
| 5,147,359 | 9/1992 | Cozad et al. . |
| 5,147,361 | 9/1992 | Ojima et al. . |
| 5,171,279 | 12/1992 | Mathews . |
| 5,180,381 | 1/1993 | Aust et al. . |
| 5,180,393 | 1/1993 | Commarmond . |
| 5,181,917 | 1/1993 | Rogozinski ............................... 606/61 |
| 5,196,013 | 3/1993 | Harms et al. . |
| 5,201,734 | 4/1993 | Cozad et al. . |

FOREIGN PATENT DOCUMENTS

| | | | |
|---|---|---|---|
| 1410965 | 7/1988 | U.S.S.R. ................................. 606/61 |
| 1243353 | 8/1971 | United Kingdom . |

*Primary Examiner*—Michael Powell Buiz
*Assistant Examiner*—Mark S. Leonardo
*Attorney, Agent, or Firm*—Edward S. Irons

[57] ABSTRACT

An apparatus, method and system for treating spinal conditions by moving or spatially fixing at least one vertebra relative to another vertebra. The invention includes a link member the ends of which are configured to be secured to adjacent vertebrae and which are offset from a central portion of the link member. The link members can be in the form of a C-shaped or V-shaped rod or plate to form the offset. The offset provides increased bone volume that can be used for grafts or fusion. Attachment structure in the form of bone screws, bolts, or hook members are provided to secure the link members to respective vertebrae. A plurality of link members can be connected in chain-like fashion to connect multiple points on a plurality of vertebrae even though those points are nonlinear. In another aspect of the invention, the links are pre-curved in the lateral plane for use in correcting spinal conditions or deformities.

28 Claims, 5 Drawing Sheets

APPARATUS, METHOD AND SYSTEM FOR THE TREATMENT OF SPINAL CONDITIONS

This is a continuation of application Ser. No. 08/131,947, filed Oct. 8, 1993, now abandoned.

BACKGROUND OF THE INVENTION

1. Field of the Invention

The present invention relates generally to apparatus and methods for treating and correcting spinal abnormalities or conditions, as well as for stabilizing the position of the spine and vertebrae thereof. More specifically, the present invention provides an apparatus and system which includes a plurality of links usable together under various circumstances to treat different spinal curvature conditions.

2. Description of the Relevant Art

The prior art includes many different apparatus and methods for treating spinal conditions. Known apparatus utilize elongate plate members having several aligned openings or an elongated slot therein for receiving screws or bolts that are affixed to vertebrae. The plate is secured to the screws or bolts and exerts force on the selected vertebra or vertebrae to move same into a desired position or to maintain same in a desired position. The plate also overlies the majority of the lateral bone surface of the vertebrae.

In using such known plate systems, a problem arises when the points on the vertebrae defined by the screws or bolts are not collinear, i.e., they do not lie in a straight line. This creates a problem for the physician because the openings in the plate are collinear and, therefore, the screws do not line up with the plate openings. The physician has several options to compensate for such nonalignment, all of which present additional problems themselves.

The plate can be contoured in the frontal plane to attempt to line the screws up with the plate openings. Due to the thickness and high strength of the plate, this is essentially impossible to do intraoperatively. Another option is to bend the screws or bolts so that they fit in the slots or openings in the plate. This creates an immediate high stress region in the screw or bolt which can cause failure of the same upon cyclical loading or, even worse, can lead to a fracture of the pedicle of the vertebra.

A third option is to place the screws or bolts in a less than optimum position or trajectory in the pedicle of the vertebrae so that they line up with the plate openings. This too can lead to pedicle fractures or cutout, as well as nerve root injury.

Other known apparatus for treating spinal deformities are disclosed in U.S. Pat. Nos. 5,102,412 and 5,181,917. These apparatus include elongate rod members which have vertebra engaging means secured thereto in an adjustable fashion. The apparatus can be used with bone bolts or screws, or laminar or pedicle hooks. However, the rods are essentially straight which makes utilizing nonlinear points of connection on adjacent vertebrae difficult without the use of specially formed components. In addition, spinal apparatus and systems such as those disclosed in the aforementioned patents include a large number of moving parts and therefore are inherently susceptible to malfunction.

Accordingly, there is a need in the art for a method and apparatus for treating spinal conditions which avoids the problems of the prior art, permits attachment to nonlinear points on adjacent vertebrae, and provides increased bone volume for grafts or fusion.

SUMMARY OF THE INVENTION

The present invention provides an apparatus and method for treating spinal conditions by moving a vertebra to a desired position with respect to additional vertebrae or maintaining the vertebra in the desired position.

The apparatus of the present invention includes a plurality of link members that can be secured to adjacent vertebrae in chain-like fashion utilizing pedicle bolts or screws that are not collinear with each other. The link members can be used to subdivide multiple nonlinear pedicle fixation points into units of two adjacent points which two points can be interconnected with a single link member.

The present invention thus facilitates multiple point fixation using two points at a time to overcome the problem in the prior art of nonalignment between plate openings and pedicle screws. The links form a chain and once they are secured to the pedicle screw or bolt with a locking nut, the result is a rigid construct securely affixed to the vertebrae.

The link members are in the form of plates or rods with opposite end portions and a central portion. The opposite end portions each have an aperture therein configured to receive attachment means affixed to the pedicle of adjacent vertebrae. The central portion of each link member is preferably offset from the end portions so that when the link member is attached to adjacent vertebrae portions of the latter are substantially uncovered by the link central portion. However, the present invention also includes links in which the central portion is not offset.

This offset provides increased vertebrae bone volume as compared with prior art apparatus which overlie the vertebra surface, which increased bone volume can be used for bone grafts and fusion. In addition, the present invention permits visualization of bony maturation using plain X-rays since the links do not overlie the graft area.

The links of the present invention can be used with and secured to pedicle screws, bolts, or pedicle or laminar hooks. A combination of hooks and screws or bolts can be used as well depending on the particular application of the invention. For example, a laminar hook can be used on a lamina that is being fused to avoid damaging its associated facet (joint) such as would be caused by a screw or bolt.

The surface of the link member of the present invention is preferably provided adjacent the apertures in the end portions thereof with radial cuts or other means for enhancing the locking engagement of the links with a pedicle bolt, screw, hook, or other link(s). The bolt or hook has a threaded extension portion that cooperates with a locking nut, and a wedge-shaped washer if needed, to secure an end of the link member to a vertebra.

The wedge-shaped washer compensates for a lack of parallelism in the axial plane between adjacent bolts or screws.

An additional aspect of the present invention is that link members can be used to secure contralateral chains (formed as described above) to each other at their ends, and/or points intermediate their ends, to form a quadrilateral or ladder-shaped construct having increased torsional stability.

BRIEF DESCRIPTION OF THE DRAWINGS

Additional features of the present invention will be apparent to those skilled in the art from the following detailed description when considered in conjunction with the accompanying drawings, wherein.

DETAILED DESCRIPTION OF THE PREFERRED EMBODIMENTS

Figure 1A:
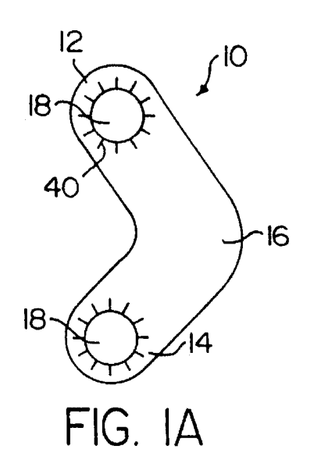
FIG. 1A is a front elevational view of a link member according to a first embodiment of the present invention.

With reference to FIG. 1A, a link member according to a first embodiment of the present invention is indicated generally by the reference numeral 10 and includes first and second end portions 12, 14 and a central portion 16. The end portions 12, 14 each have an aperture 18 therein which apertures are configured to receive a threaded bone bolt or screw, or a laminar or pedicle hook, to secure the link 10 to adjacent vertebrae as will be described below. The link 10 is preferably integrally formed so as to comprise a one-piece structure. The link in the embodiment of FIG. 1A is in the form of a plate and is substantially V-shaped with the central portion 16 comprising the apex of the V shape.

Figure 1B:
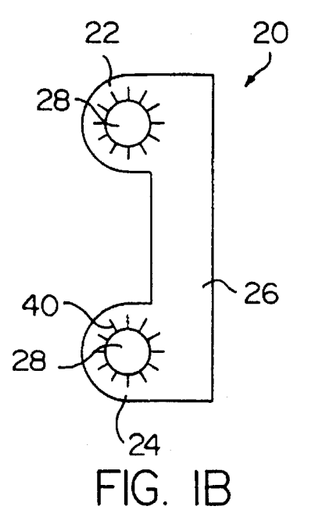
FIG. 1B is a front elevational view of a link member according to another embodiment of the present invention.

FIG. 1B shows another embodiment of the link according to the present invention indicated generally at 20. Link 20 includes first and second end portions 22, 24 and a straight central portion 26. The end portions 22, 24 each have an aperture 28 similar to the apertures 18 in link 10. Link 20 also is in the form of a plate which plate is substantially C-shaped. The C-shape of link 20, like the V-shape of the link 10 shown in FIG. 1A, provides the link with end portions that are offset from the central portion for reasons discussed below.

Figure 1C:
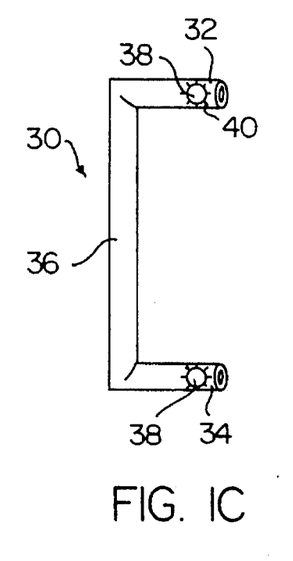
FIG. 1C is a front elevational view of a link member according to another embodiment of the present invention.

FIG. 1C shows another embodiment of a link according to the present invention which link is indicated at 30 and includes end portions 32, 34 and central portion 36. The link 30 is in the form of a C-shaped rod member having a cylindrical cross-section. It will be appreciated that the cross-sectional shape of link 30 can be non-cylindrical and that link 30 can be a rod member that is V-shaped similar to link 10 in FIG. 1A. The ends 32, 34 have an aperture 38 disposed therein for receiving pedicle bolts, screws or hooks as in the aforementioned embodiments for reasons as will be described below. The ends of the links 10, 20 and 30 have radial cuts 40 or other means for enhancing the locking engagement of the links with a pedicle bolt, screw, hook, or other link(s).

The present invention also includes link members in which the end portions and the central portion are aligned, i.e., not offset, which links can be connected in chain-like fashion to follow a nonlinear path. For example, see links 240 in FIG. 5. In an alternative embodiment, the non-offset links can be in the form of a rod with a cylindrical or noncylindrical cross-section or, the links can be in the form of other suitably shaped structure.

However, the links preferably have the respective end portions offset from the central portion as in links 10, 20 and 30. This offset is formed such that a line passing through the midpoint of the apertures formed in the end portions of links 10, 20 and 30 does not overlie the central portion of the link. See the dashed line in FIGS. 1A or 1C. While the illustrated links are V-shaped and C-shaped, those of ordinary skill in the art will recognize that other shapes are possible as long as the central portion of the link is at least partially offset from the end portions thereof.

Figure 5:
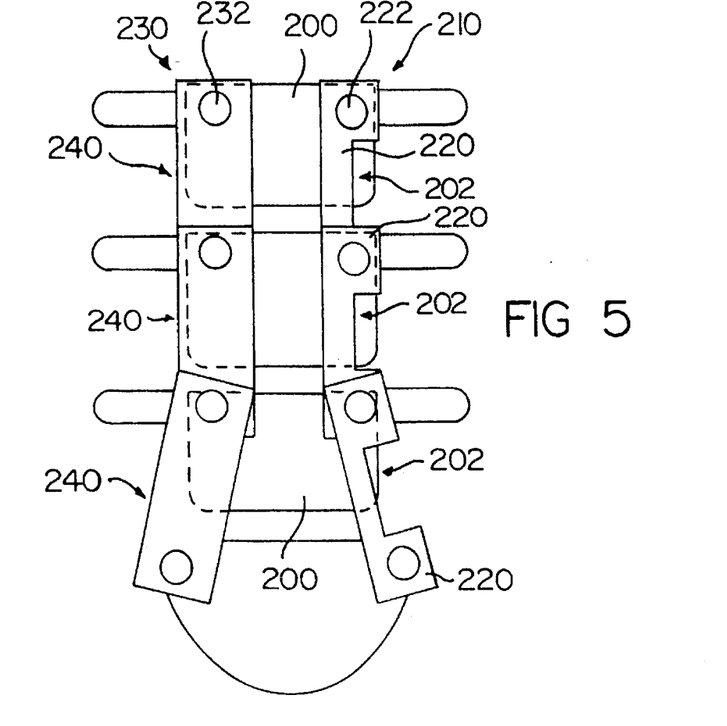
FIG. 5 is a front elevational view showing a plurality of the link members depicted in FIG. 1B, comparing them to link members in which the central portion is not offset.

FIG. 5 shows two rigid constructs 210, 230 formed of a plurality of links 220, 240, respectively. Constructs 210 and 230 are secured to the plurality of vertebrae 200 by means indicated schematically at 222 and 232, respectively. The securing means can be in the form of bone screws, bolts or hook members as will be explained in detail below. Links 220 of construct 210 have an offset central portion which leaves the lateral margin 202 on one side of the vertebrae 200 (to which the links are secured) substantially uncovered. However, links 240 of construct 230 do not have such an offset and thus the lateral margins on that side of vertebrae 200 are covered by the links 230.

The offset links 220 provide additional bone volume or surface that can be used for grafts, fusion, etc. In addition, because the bone surface is uncovered, a physician can view the bony maturation of the vertebrae being treated with plain X-rays. This is very difficult in prior art systems in which the elongated plates or rods overlie the graft area.

Figure 2:
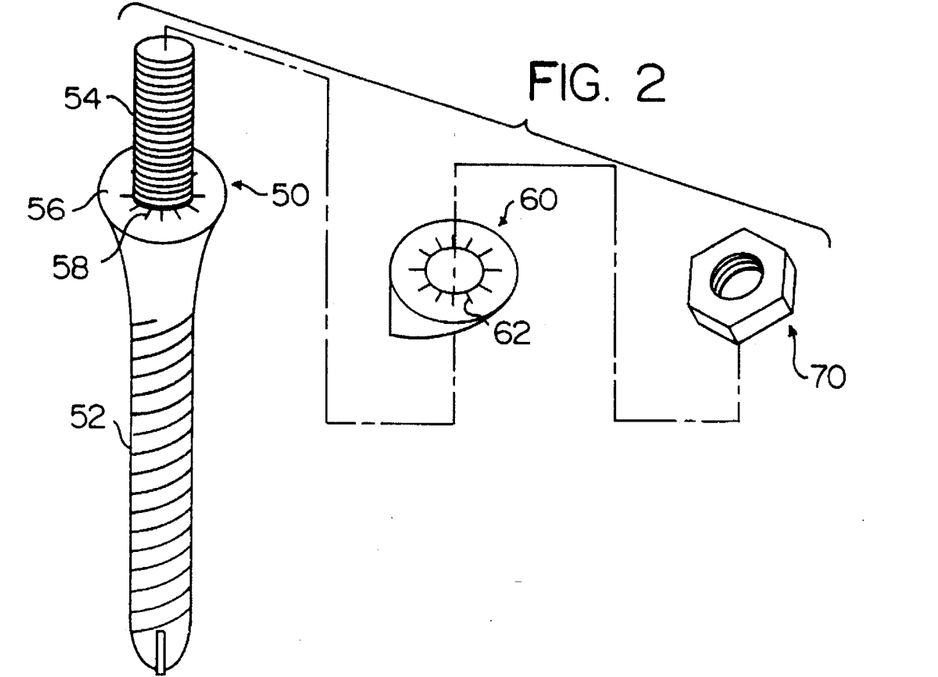
FIG. 2 is an exploded view of a pedicle or bone bolt, a washer, and a locking nut according to the present invention.

FIG. 2 shows a pedicle or bone bolt 50 used with the link members of the present invention to secure the same to vertebrae. While FIG. 2 shows a bone bolt, it will be recognized that a bone screw, e.g. a threaded member having a head which forces the link member against the bone surface, can also be used. The use of bone bolts and screws to secure spinal curvature apparatus to vertebrae by placing the same in bores formed in the vertebrae is generally known and will not be described in detail. As will be discussed below, it is also possible to use laminar or pedicle hook members in place of or in combination with the bone bolts or screws. The engagement of such attachment members with vertebrae is discussed in aforementioned U.S. Pat. Nos. 5,102,412 and 5,181,917 granted to the present applicant, the subject matter of which patents is incorporated herein by reference.

The bone bolt 50 shown in FIG. 2 includes a helical portion 52, i.e., a portion having a helical thread or cutting surface for locking the bolt within a bore formed in a vertebra (not shown). An upper portion 54 of bolt 50 is threaded to receive a locking nut such as that shown at reference numeral 70 in FIG. 2. A shoulder portion 56 is disposed between the aforementioned portions 52 and 54.

After determining the proper position on the vertebrae, a bore is formed for each bolt as is known in the art and the bolt 50 is secured to a first vertebra (not shown) with shoulder 56 and threaded portion 54 extending therefrom. The apertured end of a link member (e.g., link members 10, 20 or 30) is positioned over the threaded portion 54 with the link member resting on shoulder 56. The shoulder 56 is provided with means for enhancing the engagement between the link member and the bone screw which means can be in the form of radial cuts 58, or any other suitable means such as roughened surfaces that aids in locking the link to the screw. With one end of the link member fastened to a first vertebra, the other end of the link member is positioned on a bolt 50 that is similarly secured to a second adjacent vertebra so as to move or lock one vertebra relative to the other vertebra.

A washer member 60 is shown which preferably is wedge-shaped and is configured to slide over the threaded portion 54 of bone bolt 50. The wedge shaped washer 60 can be used to secure a link member (not shown in FIG. 2) to a bolt, screw or hook member that is attached to a vertebra and forms an angle therewith. The washer 60 is placed on the shoulder 56 so that the link member forms substantially a right angle with the longitudinal axis of the bone bolt. Locking nut 70 is then threaded over portion 54 of bolt 50. The washer member 60 also preferably has radial cuts 62 or other means for rotationally locking the link to the washer to provide overall torsional stability to the assembly.

Figure 4:
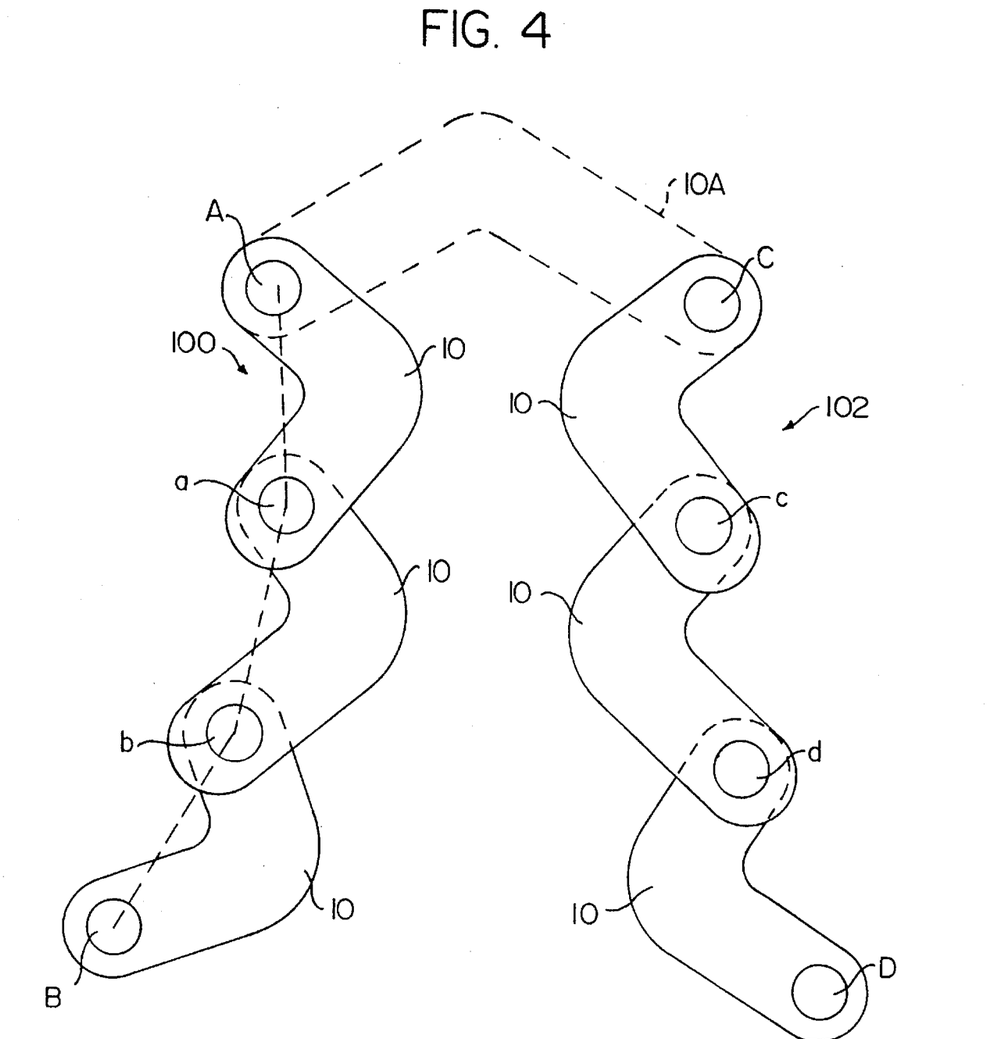
FIG. 4 is a front elevational view showing a plurality of the link members depicted in FIG. 1A placed together to form a chain-like construct.

FIG. 4 shows rigid constructs 100 and 102 formed of a plurality of link members 10 secured to each other in chain-like fashion. As seen therein, the links 10 are positioned with the end of one link overlying the end of an adjacent link. As also seen therein with respect to the construct 100 (on the left hand side of FIG. 4), a line passing through the midpoints of connection points A, a, b and B does not follow a linear path. The same is true with regard to the construct 102 and connection points C, c, d and D.

It is apparent that the aforementioned four connection points of either construct 100 or 102 are nonlinear and could not be connected using a conventional flat plate with a plurality of, e.g. four, linearly aligned openings. The same is true with regard to a prior art plate having an elongated linear slot or opening in which is positioned a plurality of bone bolts or other attachment structure. It will, of course, be recognized that the four connection points depicted in FIG. 4 are for exemplary purposes only and that it is possible to use more or less vertebrae attachment points. This aspect of the present invention permits a rigid construct to be formed using multiple vertebrae attachment points notwithstanding the fact those points do not lie in a straight line. This was not possible with prior art plates having linearly aligned multiple openings.

Also shown in FIG. 4 is a link member 10A, depicted in phantom, which serves as a cross-tie mechanism that secures the distal most connection points A and C of the constructs 100 and 102, respectively. While not shown in FIG. 4, a link member preferably is used on the opposite distal end points B and D. This results in a quadrilateral construct that stabilizes the chain-like construct both torsionally and in the frontal plane, as well as increases the strength required to pull the screws out of the vertebrae. Further, such cross-tie mechanisms can be used as well at points intermediate the distal most connection points of the chain-like constructs.

Figure 6:
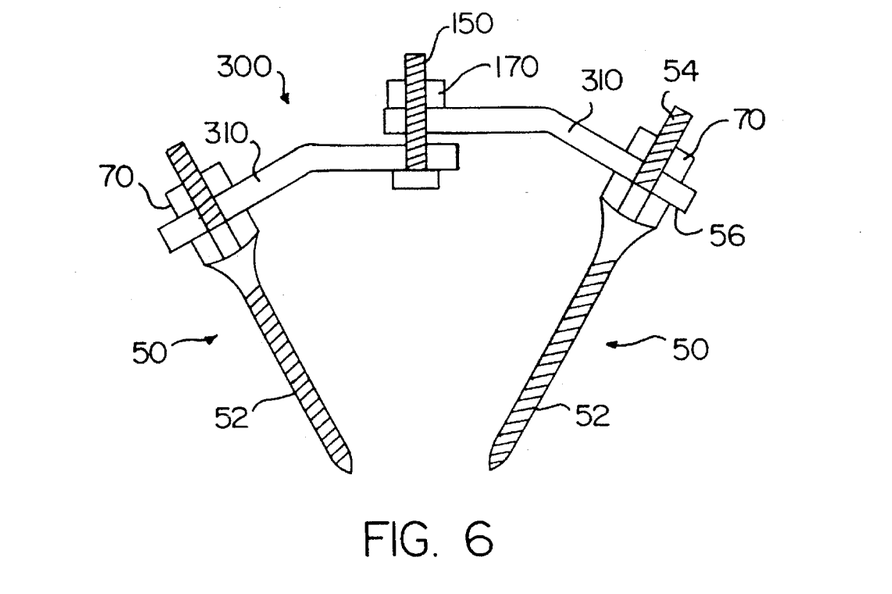
FIG. 6 is a side elevational view, partly in section, showing two bone bolts and a locking bolt securing together two link members in a delta configuration according to the present invention.

A further embodiment of the present invention is shown in FIG. 6 and includes a cross-tie mechanism 300 to provide a quadrilateral construct similar to that discussed above. The cross-tie mechanism 300 includes two links 310 that are produced according to the teachings of the present invention which links are secured to respective bolts 50 substantially as described above. That is, locking nuts 70 cooperate with threaded portions 54 of bolts 50 to attach the latter to the links 310.

The ends of the links 310 opposite bone bolts 50 are secured to each other by a locking bolt 150 and nut 170. The ends of the links 310 are overlapped on the bolt 150 and the nut 170 is threaded over and secured to the bolt 150 to lock the entire assembly. The cross-tie mechanism 300 provides a rigid quadrilateral construct which increases the torsional stability and pull-out strength. As seen in FIG. 6, bone bolts 50 are disposed in respective vertebrae (not shown) in a converging fashion which, when combined with a cross-tie mechanism, provide a configuration which increases the overall pull-out strength of the assembly. The cross-tie mechanism 300 also can be used at different locations along the length of the two constructs to form a ladder configuration.

Figure 3:
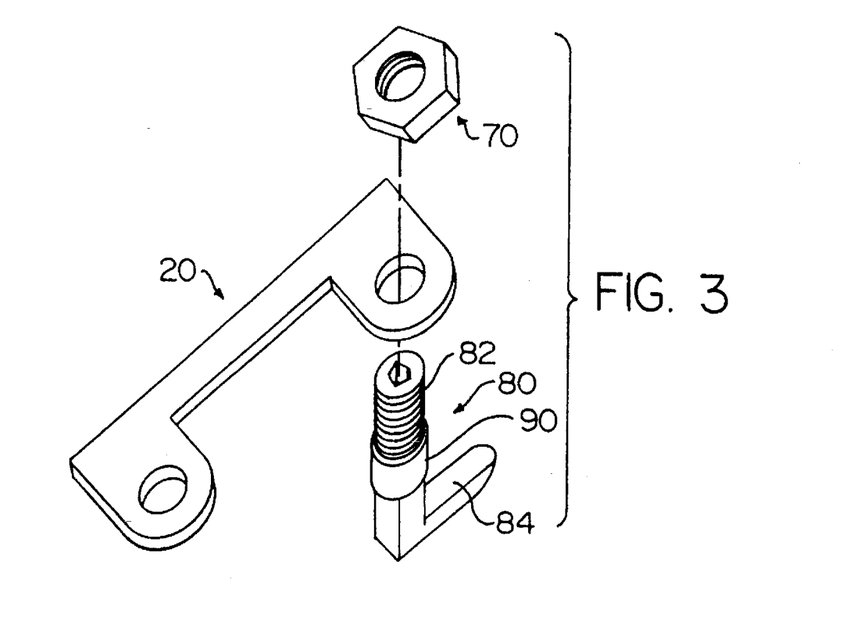
FIG. 3 is an exploded view of a pedicle or laminar hook, the link shown in FIG. 1B, and a locking nut according to another embodiment of the present invention.

With reference to FIG. 3, a laminar hook 80 is shown which can be used in addition to or in place of the bone bolts 50 of FIG. 2. While member 80 is referred to as a laminar hook, those skilled in the art will appreciate that pedicle hooks could be utilized as well. Laminar hook 80 includes a hook or pad portion 84 which engages portions of the lamina of a respective vertebra. It will be appreciated that the hook portion 84 can be in a form other than the L-shape shown in FIG. 3 and, for example, can take the shapes shown in the aforementioned patents incorporated by reference in this application.

Hook member 80 further includes a threaded upper bolt portion 82 which is passed through the aforementioned aperture in one end of a link member, which link in FIG. 3 is in the form of the C-shaped plate member 20 (of FIG. 1B). Locking bolt 70 is then threaded onto portion 82 of hook member 80 to securely lock the link 20 to the vertebra.

FIG. 3 also shows a sleeve member 90 which is disposed over threaded portion 82 of hook 80 to adjust the height of the link member 20 with respect to the hook or pad portion 84. The proper height sleeve needed for a particular application will typically depend on the laminar thickness of a vertebra and will be determined intraoperatively by the surgeon. The sleeve 90 preferably will be provided in different sizes so that the surgeon can choose the proper size sleeve for the specific application.

Figure 7:
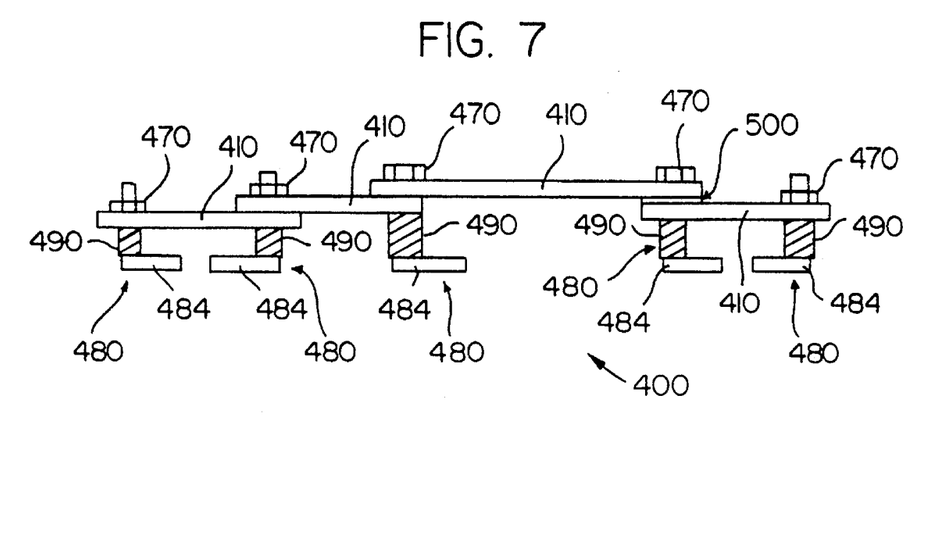
FIG. 7 is a side elevational view showing a plurality of link members according to the present invention secured together by pedicle or laminar hook members and locking nuts.

With attention now directed to FIG. 7, a side elevational view of an exemplary rigid construct assembled from a plurality of link members in accordance with the present invention is indicated generally by reference numeral 400. The construct includes a plurality of links 410 connected end-to-end in chain-like fashion as described above. The construct 400 includes laminar or pedicle hooks 480 but it will be understood that the above-described bone bolts or screws can be used in addition to or in place of the hooks 480.

As shown in FIG. 7, sleeves 490 of various heights are interposed between the hook or pad portion 484 of each the hooks 480 and link members 410. In addition, a spacer member 500 is disposed between the two adjacent link members 410 on the right end of the construct to compensate for the difference in height thereof so as to permit the links to be connected substantially in parallel. The aforementioned means for enhancing the locking relationship, e.g., roughening or radial cuts, between the bolts or hooks and the links, the locking nuts 470 and bolts, between adjacent links, etc., can also be used.

It will be readily recognized that the construct shown in FIG. 7 is but one example of an application of the present invention. In addition, it will be appreciated that FIG. 7 shows a construct that can be connected to a similar construct by any of the aforementioned cross-tie mechanisms to provide a quadrilateral construct.

Figure 8A:
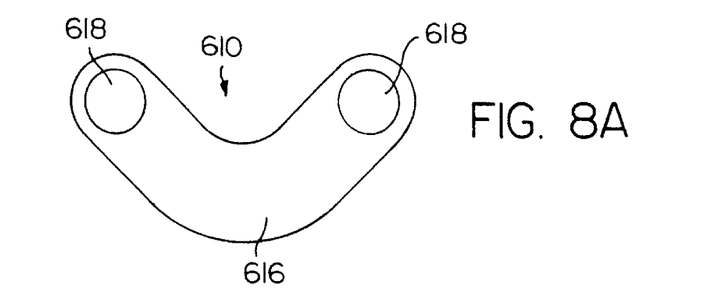
FIGS. 8A and 8B are, respectively, front and side elevational views of a curved link member according to another embodiment of the present invention.
Figure 8B:
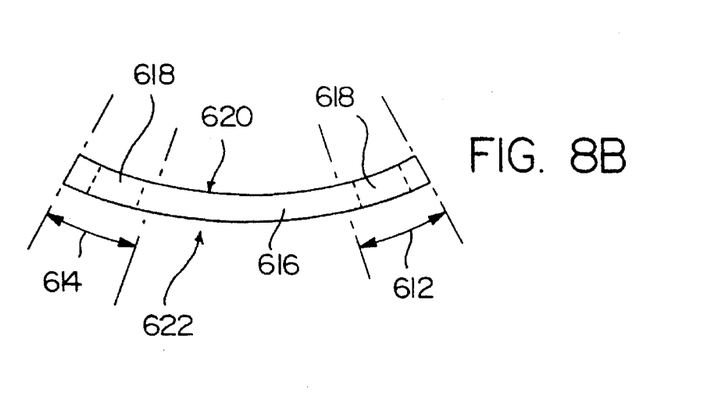

Another aspect of the present invention is shown in FIGS. 8A and 8B and includes link members which are pre-curved in the sagittal or lateral plane for treating various spinal conditions. The link 610 is plate-shaped and is similar to link 10 except that link 610 is pre-curved in the sagittal plane. As can be seen, concave and convex surfaces 620 and 622 are defined on opposite sides of link 610. FIGS. 8A and 8B show that the plane in which the link is pre-curved is substantially perpendicular to the plane in which the link is offset, i.e., the plane in which central portion 616 is offset from the ends 612, 614.

While link 610 is plate shaped, the present invention also includes rod-shaped links (as described above and shown in FIG. 1C) which are pre-curved in a similar fashion. The end portions 612, 614 of link 610 are preferably flat so that apertures 618 properly engage the vertebrae attachment members. However, the entire link (and not just central portion 616) can be curved instead.

For example, the link 610 can be placed as shown in FIGS. 8A and 8B to treat lordosis (forward curvature of the lumbar or thoracic spine), while the link could be placed in reverse to treat kyphosis (backward convex curvature of the spine). It will be appreciated that pre-curving the links in a manner other than that shown in FIGS. 8A and 8B is possible to achieve links having shapes and/or curvatures suited for additional applications.

The pre-curved links made according to the present invention provide the surgeon with numerous curved spinal links from which can be selected the appropriate link member for a particular application. This is superior to the flat prior art links. The curvature of the present links is set during manufacturing by any suitable process, e.g. a forming or machining process, and thus the link curvature is precise and results in efficient application of force to the selected vertebrae.

It is apparent that the present invention provides a link member that can be secured to other link members in chain-like fashion so as to permit connection of a series of points forming a nonlinear path on several vertebrae. In this manner, force can be selectively exerted on a particular vertebra or vertebrae to move the vertebra to a desired position and to maintain same in that position.

The present invention also includes links which overcome the problem with prior art plate systems in which minimal bone volume is available for grafts or fusion by providing an offset link structure. According to one aspect of the present invention, the central portion of the link is laterally displaced relative to the end portions thereof so as to leave the surface of the lateral margin of a vertebra to which the link is attached substantially uncovered.

Although the invention has been described with reference to particular embodiments, it is to be understood that the embodiments are merely illustrative of the application of the principles of the invention. Numerous configurations may be made therewith and other arrangements may be devised without departing from the spirit and scope of the invention.

What is claimed is:

1. A method for treating spinal conditions by spatially fixing at least a first vertebra relative to a second vertebra while leaving exposed at least a lateral marginal area of the lamina of one of said vertebrae, the method including steps of:

fixing a first attachment member to the first vertebra at a selected position;

fixing a second attachment member to the second vertebra at a selected position;

providing at least one one-piece spinal implant link member in the form of a substantially flat plate having an apertured first end, an apertured second end, and an offset middle portion, the first and second ends of the link member defining an open space therebetween which space is disposed adjacent the middle portion and extends away from the middle portion;

attaching said first end of said at least one link member to said first attachment member which is fixed to the first vertebra by placing the aperture in said first end around the first attachment member; and attaching said second end of said at least one link member to said second attachment member which is fixed to the second vertebra by placing the aperture in said second end around the second attachment member, so that a force is exerted on the first vertebra by said at least one link member;

whereby a lateral marginal area of the lamina of one of said vertebrae is exposed by said space of said link member and provides an area for performing a bone graft.

2. The method of claim 1, wherein one of the steps of respectively fixing the first and second attachment members to the first and second vertebra includes fixing a threaded bolt to the vertebra, and said at least one link member is attached to the bolt by placing one of the apertured ends of the link member on said bolt and placing a locking nut over the link member.

3. The method of claim 1, wherein said at least one link member is V-shaped such that said ends are laterally offset from the middle portion so as to expose surface area of the vertebrae to which the link member is attached.

4. The method of claim 1, further including the step of securing a second link member to a third vertebra and to one of said first and second vertebrae, the second link member being secured to one of the first and second vertebrae by attaching an end of the second link member to one of said first and second attachment members so as to overlie an end of said at least one link member and extend away from said end of the at least one link member, said second link member then being secured to a third attachment member which is secured to the third vertebra.

5. A system for treating spinal conditions such as spinal instability and deformities by applying force to selected vertebrae, the system comprising:

a plurality of links each configured to be secured to adjacent vertebrae to exert a desired force on at least one vertebra;

each link being in the form of a one-piece member having opposite ends with an aperture in each end, and a central portion extending between said opposite ends, each of said opposite ends having means for locking the end of one link to the end of another link at various desired angular positions with the end of one link overlying and abutting the end of an adjacent link;

said plurality of links being configured for attachment to each other with one of said opposite ends of a first link overlying and abutting one of said opposite ends of a second link to form a linked construct that extends between two distal points on said vertebrae, the individual links of said plurality of links each being connectible to selected points on adjacent vertebrae so as to permit said linked construct to follow a nonlinear path between said two distal points; and means for securing each of said plurality of links to adjacent vertebrae and to at least one additional link of said plurality to form said linked construct which exerts the desired force on said selected vertebrae.

6. A system for treating spinal conditions according to claim 5, wherein the securing means are attachment members configured to be fixed to respective vertebrae and for receiving the ends of respective links in locking engagement, and further including means for locking the respective links to the attachment members.

7. A system for treating spinal conditions according to claim 6, wherein at least some of said plurality of links have an offset middle portion between said first and second ends.

8. A system for treating spinal conditions according to claim 7, wherein said links having an offset middle portion are C-shaped plate members.

9. A system for treating spinal conditions according to claim 7, wherein said links having an offset middle portion are rod members.

10. A system for treating spinal conditions according to claim 7, wherein said links having an offset middle portion are V-shaped plate members.

11. An apparatus for treating spinal conditions and for being attached to adjacent vertebrae so as to exert a force on said vertebrae while exposing a surface of one of the vertebrae which is usable for a bone graft or fusion, the apparatus comprising:

means for connecting a first vertebra to a second vertebra, said means including a one-piece link member having opposite ends and a central portion connecting said opposite ends, the opposite ends each having an aperture therein configured to receive an attachment device for respectively attaching the opposite ends of the link member to the first and second vertebrae; and wherein the central portion of said link member is offset from said opposite ends of the link member and disposed away from a line connecting the midpoints of said apertures in a direction which is transverse to said line to define an open space between said opposite ends;

wherein said link member is curved in a first plane such that a first surface of the link member is substantially convex shaped and a second surface of the link member is substantially concave shaped, and wherein said ends of the link member are substantially flat and said substantially convex and concave surfaces extend between the ends;

whereby when said link member is attached to the respective vertebrae a lateral margin of one of said vertebrae is substantially uncovered within said open space to provide bone volume that can be used for bone grafts or fusion.

12. An apparatus for treating spinal conditions according to claim 11, wherein the central portion of said link member is offset in a second plane that is substantially perpendicular to said first plane.

13. An apparatus for treating spinal conditions according to claim 11, wherein said link member is plate-shaped.

14. An apparatus for spatially fixing a first vertebra with respect to a second vertebra, the apparatus comprising:

a plurality of hook members each configured to engage the lamina of a vertebra, each hook member being substantially L-shaped and including a pad portion connected to an extended portion, the pad portion extending transversely and substantially horizontally from the extended portion, the pad portion having an upper surface defining a support for receiving a lamina of a vertebra, wherein the extended portion comprises a threaded shaft which extends upwardly from said transverse pad portion in a substantially vertical direction, the extended portion and the transverse pad portion forming the L-shape of said hook member, said extended portion being configured to receive a spinal fixation device so that said device is spaced from the pad portion of said hook member with a lamina of a vertebra captured therebetween; and at least one spinal fixation device having opposite ends with an opening in each of said ends for receiving therein the extended portion of one of the hook members;

whereby a first hook member may be positioned on the lamina of a first vertebra and a second hook member may be positioned on the lamina of a second vertebra, and the opposite ends of the spinal fixation device may be positioned, respectively, on the extended portions of the first and second hook members to connect the first and second hook members.

15. An apparatus according to claim 14, further including a plurality of spacer sleeves each being configured for placement on the extended portion of a respective hook member so as to space the spinal fixation device from the pad portion of the hook member.

16. An apparatus according to claim 15, wherein said plurality of spacer sleeves include sleeves having various lengths for forming various length spaces between the pad portion of a hook member and a spinal fixation device.

17. An apparatus according to claim 14, wherein said at least one spinal fixation device is a link member comprising:

an integral structure including opposite ends and a central portion connecting said opposite ends, the opposite ends each having an aperture therein configured to receive means for attaching the link to respective vertebrae; and wherein the central portion of said link member is offset from said opposite ends of the link member such that a line passing through the midpoint of each said aperture is laterally spaced from said central portion of the link member so that when said link member is attached to the respective vertebrae a lateral margin of one of said vertebrae is substantially uncovered to provide bone volume that can be used for bone grafts or fusion.

18. A method for treating spinal conditions by spatially fixing at least a first vertebra relative to a second vertebra while leaving exposed at least a lateral marginal area of the lamina of one of said vertebrae, the method including steps of:

(a) positioning a first laminar hook member on the first vertebra at a selected position;

(b) positioning a second laminar hook member on the first vertebra at another selected position;

(c) providing at least first and second one-piece spinal implant link members, each member having an apertured first end, an apertured second end, and an offset middle portion, the first and second ends of each link member defining a space therebetween which space is disposed adjacent the middle portion and extends away from the middle portion to a line connecting the apertures in the ends of each link member;

(d) attaching the first end of said first link member to the first laminar hook member and attaching the second end of said first link member to the second laminar hook member to capture a portion of the first vertebra between the respective hook members;

(e) attaching one end of the second link member to the second vertebra; and (f) attaching the first link member to the second link member with one of the ends of the first link member overlying the other end of the second link member;

whereby a lateral marginal area of the lamina of one of said vertebra is exposed by the space defined by the offset middle portion of at least one of the link members to provide an area for performing a bone graft.

19. A method for treating spinal conditions according to claim 18, further including the step of positioning a spacer sleeve on at least one of the hook members before carrying out step (d), to locate the first link member at a desired position on the one hook member.

20. An apparatus for treating spinal conditions by spatially fixing a first vertebra with respect to additional vertebrae, the apparatus comprising:

a plurality of attachment members each of which has means for being attached to a vertebra;

a plurality of link members each adapted to be secured to adjacent vertebrae, each link member being a one-piece, substantially V-shaped flat plate having opposite ends and a central portion connecting said ends, the opposite ends each having an aperture therein configured to receive the attachment members to secure the link member to said adjacent vertebrae;

the central portion of each of said plurality of link members being offset from said opposite ends of the link member and forming the apex of the V-shaped flat plate while defining a space between said opposite ends; and wherein the opposite ends of each link member have means for locking the end of a first link to the end of a second link at various desired angular positions with the end of the first link overlying and abutting the end of the second link;

whereby when one of the link members is fixed to adjacent vertebra, a portion of the surface of at least one of the vertebrae is exposed in the space between the opposite ends of the link member to provide a surface that can be utilized for a bone graft.

21. An apparatus according to claim 20, wherein said plurality of attachment members include at least one laminar hook member, said hook member being substantially L-shaped and including a pad portion extending transversely from an extended portion, the extended portion including a threaded shaft which forms along with the pad portion the L-shape of said hook member, the extended portion being configured to be received in one of the apertures of one of said link members to capture a lamina of one of said vertebrae between the pad portion and the link member.

22. An apparatus according to claim 20, wherein said attachment members are bone bolts each having at one end thereof a helical portion adapted to be fixed in bores disposed in respective vertebrae, and at an opposite end thereof a threaded portion which protrudes away from a vertebra when the bone screw is fixed thereto, the threaded portion being configured to engage one of the apertured ends of one of said link members.

23. An apparatus according to claim 22, further including locking nuts configured to be positioned over one of the link members on the threaded portion of one of the bone bolts to securely fix the link member to the bone bolt.

24. An apparatus according to claim 22, wherein each bone bolt has an annular shoulder formed between the threaded portion and the helical portion for supporting an end of one of said link members, said shoulder being provided with means for enhancing the engagement of the link member with the bone bolt.

25. An apparatus according to claim 24, further including at least one washer member configured to be positioned on the bone bolt between the vertebra and the link member, said washer being wedge-shaped so that the link member can be secured to the bone bolt at an angle of substantially 90°.

26. An apparatus for treating spinal conditions by spatially fixing a first vertebra with respect to additional vertebrae, the apparatus comprising:

a plurality of attachment members each of which has means for being attached to a vertebra;

a plurality of link members each adapted to be secured to adjacent vertebrae, each link member being a one-piece, substantially C-shaped flat plate having opposite ends and a straight central portion connecting said opposite ends, with the opposite ends extending away from the straight central portion, each of the opposite ends having an aperture therein configured to receive the attachment members to secure the link member to said adjacent vertebrae;

the straight central portion of each of said plurality of link members being offset from said opposite ends of the link member and defining a space between said opposite ends; and wherein the opposite ends of each link member have means for locking the end of a first link to the end of a second link at various desired angular positions with the end of the first link overlying and abutting the end of the second link;

whereby when one of the link members is fixed to adjacent vertebra, a portion of the surface of at least one of the vertebrae is exposed in the space between the opposite ends of the link member to provide a surface that can be utilized for a bone graft.

27. An apparatus for treating spinal conditions by spatially fixing a first vertebra with respect to additional vertebrae, the apparatus comprising:

a plurality of attachment members each of which has means for being attached to a vertebra;

a plurality of link members each adapted to be secured to adjacent vertebrae, each link member being a one-piece, substantially V-shaped rod having opposite ends and a central portion connecting said ends, the opposite ends each having an aperture therein configured to receive the attachment members to secure the link member to said adjacent vertebrae;

the central portion of each of said plurality of link members being offset from said opposite ends of the link member and forming the apex of the V-shaped rod while defining a space between said opposite ends; and wherein the opposite ends of each link member have means for locking the end of a first link to the end of a second link at various desired angular positions with the end of the first link overlying and abutting the end of the second link;

whereby when one of the link members is fixed to adjacent vertebra, a portion of the surface of at least one of the vertebrae is exposed in the space between the opposite ends of the link member to provide a surface that can be utilized for a bone graft.

28. An apparatus for treating spinal conditions by spatially fixing a first vertebra with respect to additional vertebrae, the apparatus comprising:

a plurality of attachment members each of which has means for being attached to a vertebra;

a plurality of link members each adapted to be secured to adjacent vertebrae, each link member being a ,one-piece, substantially C-shaped rod having opposite ends and a straight central portion connecting said opposite ends, with the opposite ends extending away from the straight central portion, each of the opposite ends having an aperture therein configured to receive the attachment members to secure the link member to said adjacent vertebrae;

the straight central portion of each of said plurality of link members being offset from said opposite ends of the link member and defining a space between said opposite ends; and wherein the opposite ends of each link member have means for locking the end of a first link to the end of a second link at various desired angular positions with the end of the first link overlying and abutting the end of the second link;

whereby when one of the link members is fixed to adjacent vertebra, a portion of the surface of at least one of the vertebrae is exposed in the space between the opposite ends of the link member to provide a surface that can be utilized for a bone graft.

* * * * *